United States Patent
Aichert et al.

(10) Patent No.: US 6,372,505 B1
(45) Date of Patent: Apr. 16, 2002

(54) PROCESS AND APPARATUS FOR TITRATING

(75) Inventors: Albert Aichert, Dürnten; Gregor Amrein, Baden, both of (CH)

(73) Assignee: Mehler-Toledo GmbH, Greifensee (CH)

( * ) Notice: Subject to any disclaimer, the term of this patent is extended or adjusted under 35 U.S.C. 154(b) by 0 days.

(21) Appl. No.: 09/426,906

(22) Filed: Oct. 26, 1999

(30) Foreign Application Priority Data

Nov. 3, 1998 (CH) .............................................. 2116/98

(51) Int. Cl.$^7$ .............................................. G01N 31/16
(52) U.S. Cl. .............................. 436/51; 422/75; 422/77; 436/42; 436/163; 700/50; 700/267; 702/25; 702/31
(58) Field of Search .............................. 436/39, 42, 51, 436/163, 150, 151; 422/75, 76, 77, 82.01–82.03; 700/46, 50, 267; 702/25, 31

(56) References Cited

U.S. PATENT DOCUMENTS

| | | | | |
|---|---|---|---|---|
| 3,870,466 | A | * | 3/1975 | Rellstab et al. |
| 4,180,440 | A | * | 12/1979 | Gibboney et al. |
| 5,291,418 | A | * | 3/1994 | Sanders et al. |
| 5,618,495 | A | * | 4/1997 | Mount et al. |

FOREIGN PATENT DOCUMENTS

JP 05309376 11/1993

OTHER PUBLICATIONS

Macleod S K; "Moisture determination using Karl Fischer Titrations" Analytical Chemistry, Bd. 63, Nr. 10, May 1991.
Firstenberg S et al; "A microcomputer–based digital titrator"; International Laboratory, Bd. 8, Mar. 1978.
Metrohm Program 1996; Produkatalog, Metrohm Ionenanlytik, Metrohm AG, CH–9101 Herisau XP002130986.
Harrington, P. De B et al.; "FLIN: fuzzy linear interpolating network"; Analytica Chimica ACTA; Bd. 277, Nr. 2, May 1993.
Metrohm–Program 1996; Production Catalog Metrohm Ionenanalytik, Metrohm AG, 1996.

* cited by examiner

*Primary Examiner*—Jan Ludlow
(74) *Attorney, Agent, or Firm*—Lawrence E. Laubscher, Sr.

(57) ABSTRACT

In a process for titrating substances by adding increments of a titrant in time intervals, the course of the reaction is monitored in its approach toward the end point (EP), and the addition of titrant is controlled. At least one differential component is determined from the course of the reaction and used for controlling the addition of titrant. The process can be performed by an apparatus that includes a delivery unit for the titrant and suitable devices for performing the monitoring, differentiating and control functions.

17 Claims, 3 Drawing Sheets

PROCESS AND APPARATUS FOR TITRATING

BACKGROUND OF THE INVENTION

1. Field of the Invention

The present invention relates to a process and apparatus for titrating substances by a stepwise addition of a discrete incremental quantity of titrant, at first in time intervals t4, then in time intervals t5, and finally in time intervals t6, while the progress of the reaction towards its end point (EP) is being monitored and the addition of titrant is being controlled. The discrete incremental quantity and the lengths of the time intervals t4, t5, t6 are the parameters that determine the speed of titration in this process.

2. Brief Description of the Prior Art

Processes of this kind are an established practice for making quantitative determinations in laboratories, and it is known that they require a certain amount of time. Not least among the reasons is the fact that the reaction gets progressively slower as it approaches the end point, which in itself may be a source of inaccuracy, as is the case if the reaction slows down so much towards the end that it appears to have reached its end point while, in fact, there is still a certain amount of "after-consumption" that is missed in the measurement. The opposite case can also occur and is known as "over-titrating". This happens if one attempts to speed up the process by adding another increment of titrant before a clear response to the previous increment has been observed, so that subsequently a surplus of titrant is registered, which degrades the accuracy of the measurement.

SUMMARY OF THE INVENTION

It is therefore the object of the present invention to improve the speed and/or the accuracy of the titration process. According to the invention, this is accomplished by controlling the addition of titrant through a control function that is formed by using at least one differential component (time derivative) of the reaction curve that is obtained by the incremental addition of titrant.

In particular, by employing the inventive concept, the stated objective is met even under difficult conditions as, e.g., in a Karl Fischer titration, where in many cases minute quantities of water have to be determined.

While it may be clear from the above discussion of the background of the invention that the discrete, individually added (incremental) quantity and the lengths of the time intervals in which such individual increments are added are determinant parameters for the speed of the titration process, those who are experienced in the practice of titration are also aware of the fact that there are additional parameters influencing the speed of the reaction and of the measurement. To be mentioned in particular among these additional parameters are the substances themselves that are to be titrated—the titrant, the solvent, and the pin length of the electrode—, but there are also further parameters that are of common knowledge to professionals in the art of titration. The mutual influence that such parameters have on each other is hard to determine, although their resultant reaction curves will generally be exponential curves in one form or another. Such curves, however, are easy to determine empirically and store in memory in order to introduce the change over the course of the reaction, i.e., its differential component (time derivative), into the mathematical function that controls the addition of titrant.

However, given the varying degree of influence that all of the parameters have on each other as well as on the course of the reaction, it has been found particularly advantageous to use a fuzzy-logic method to process the differential component. In addition to the distance from the end point at a given time, at least the differential component (in the sense of the above definition, i.e., determined from a curve or measured directly as differential component) can be entered as an input into the fuzzy logic. It is to be understood that the use of a fuzzy logic in this case represents a significant inventive concept, even without the input of a differential component, given that the process is influenced by an unknown multitude of different parameters that (after it has been recognized that they should be considered in the control function) could hardly be captured correctly through any other method of logic interconnection between them.

The preferred way of carrying out the inventive process is by using an apparatus that comprises an arrangement for performing a differentiating function capable of determining a differential component from the course of the reaction and for entering the differential component into a fuzzy-logic control module. In principle, however, the inventive process could also be carried out manually.

Further details of the invention are presented in the following description of an embodiment that is illustrated schematically in the drawing.

DETAILED DESCRIPTION OF THE INVENTION

Figure 2:
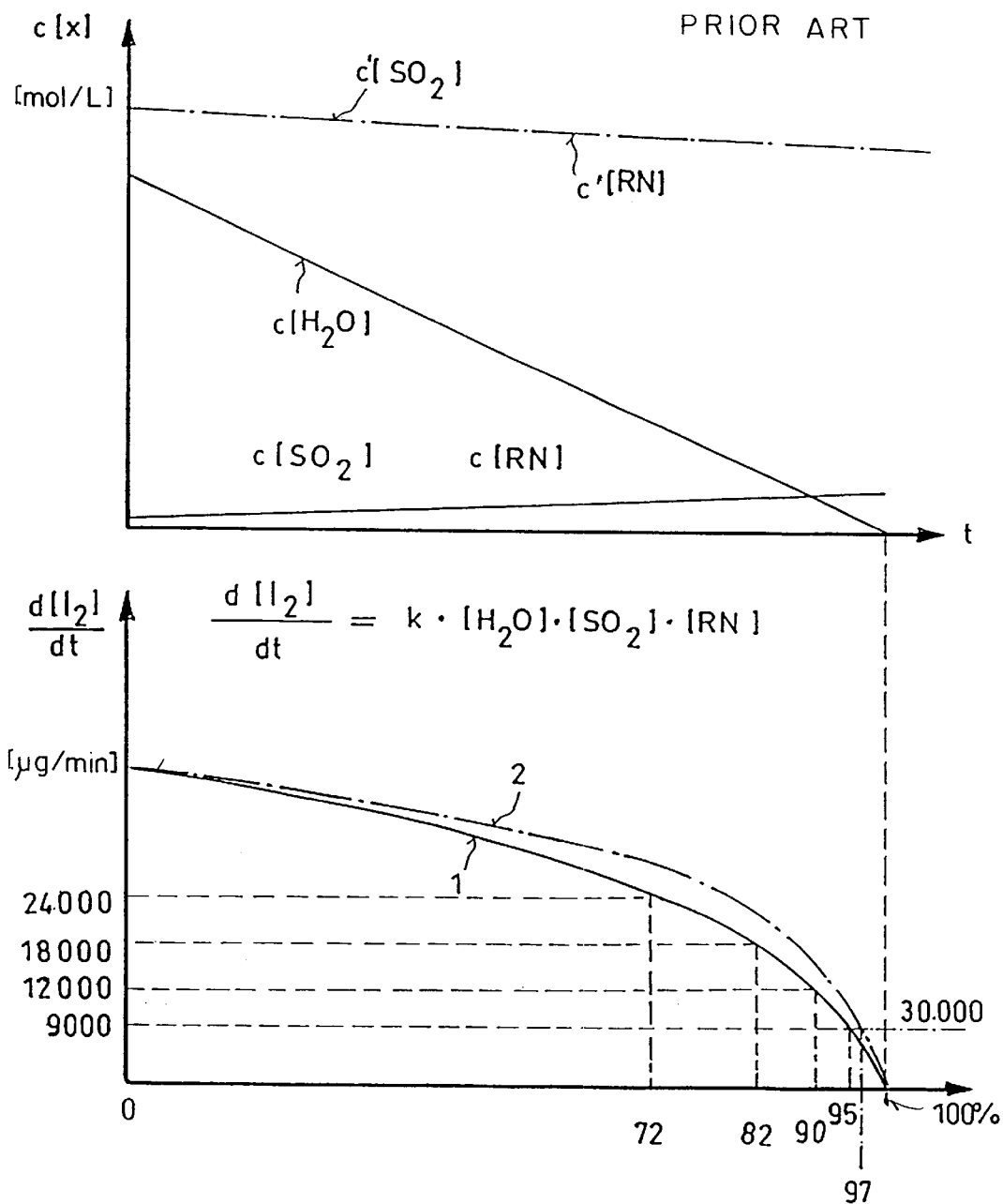
FIG. 2 represents, for comparison, a diagram to visualize the course of events in a conventional titration.

To start with a discussion of the state of the art, FIG. 2 shows two diagrams that are related to each other. The upper of the two diagrams represents the concentration in mol/L as a function of the time t. Over the course of a titration for determining the water content in a solution, the concentration of water $c[H_2O]$ decreases at a more or less uniform rate until the end point is reached at the intersection with the abscissa as illustrated by the respective straight line.

To perform the determination of the water content, a reagent is used, e.g., a mixture of RN (Chemical designation for an amine such as, e.g., imidazole), iodine and $SO_2$. The titration is carried out by adding individual quantities of RN and $SO_2$, either each of them separately as a one-component solution or after mixing the two components beforehand. In the latter case, it is common practice to use a considerable excess quantity of $SO_2$ which has the effect of speeding up the reaction, so that it runs three to four times faster than with a one-component solution. With the one-component solution, there is also a certain effect from the mixing of the components, and the general practice is to add only a slight excess quantity of $SO_2$. The formula used for determining the reaction time (wherein k represents a constant) is shown below the upper diagram of FIG. 2.

There is an essential difference between the two methods (i.e., using one-component vs. two-component solutions): As the concentration of water decreases uniformly towards the lower end point, the concentration of RN and $SO_2$ increases slightly from a low starting value, as represented by the line labeled with $c[SO_2]$ and $c[RN]$. In the case of a two-component solution, on the other hand (as represented by the dash-dotted line) the concentration c'[SO$_2$], c'[RN] starts at a high level and decreases slightly over the course of the reaction.

The point of departure for the present invention lies in the observation that the monitoring of a differential component such as the time derivative d[I$_2$]/dt over the course of the reaction is of major significance for the control of the process. As is evident from the lower diagram of FIG. 2, the magnitude of this term, expressed in $^\mu$g/min, follows a line whose curvature corresponds approximately to an exponential function. This can be explained by the fact that at the beginning, while the water concentration is high (see upper diagram), the speed of the reaction is relatively high but decreases as the end point is approached. As the respective numerical values ($^\mu$g/min) to the left and right of the lower diagram are different, it needs to be pointed out that the two curves 1 and 2 are, in reality, not at the same level but, rather, one lies above the other, i.e., they are drawn to different scales. Also, it should be noted that while the time t is indicated at the abscissa of the upper diagram, this does not refer to absolute amounts of time but to relative values expressed in relation to the decrease in water concentration. Already under the existing state of the art, the value of this decrease was used for the control of the increments, i.e., the individual amounts of titrant to be added at a given time. This was done in a form where the amount of each individual increment was controlled as a function of the distance of the line c[H$_2$O] from the end point of the reaction, i.e., the distance from the abscissa (referring to the upper diagram of FIG. 2). However, this prior-art procedure gave unsatisfactory results, as was described above in the introductory paragraph.

The curve labeled 1 in the second diagram of FIG. 2 illustrates how the reaction runs with a one-component reagent, while the curve labeled 2 is representative for a two-component titrant. Although the two curves 1 and 2 have a considerable degree of similarity, it has nevertheless been found that the process can be improved in accordance with the objective of the invention stated above by making use of curves of this type in the control of the process. According to this concept, the curves (which contain the information about the change, i.e., the differential component of the process variable) are empirically determined for a range of substances, concentrations, titrants (that differ in their chemical composition, in their concentration and in whether they are added as one- or two-component reagents), for different solvents (methanol, ethanol, formamide, chloroform, pyridine, etc.) as well as for different electrode pin lengths, electrode pin types, and other characteristics of the process, and this information is subsequently taken into account in controlling the titration. All of these parameters can cause slight changes in the shape of the curve. Notably, it has been observed that the best way to avoid the problem of "over-titrating" for one, and also the problem of inaccurate titration results, is to adapt the individually added quantities of titrant to the shape of the curve for the reaction as shown in the bottom half of FIG. 2. The method of using the aforementioned parameters in the form of, e.g., stored or graphically traced curves, however, represents only one of the possibilities of including the differential component. It is equally feasible, either as an additional or as an alternative measure, to obtain the differential component from the course of the measurement itself, i.e., from the changes occurring in the measured values, and to perform the control in the manner of a PD servo or, in some cases, a PID servo.

The inventive process follows from the conclusions that are drawn from the foregoing observations, as will now be explained on the basis of FIG. 1.

FIG. 1 is again divided into an upper and a lower diagram. In the upper diagram, the signal voltage in mV of a measuring electrode is plotted against the titration time t, with the end point indicated as a dash-dotted line. The lower diagram illustrates the volume change in $^\mu$L as a function of the time t. In order to increase the accuracy and/or to shorten the titration time, it is practical to start out with a volume increment of a preset maximum amount Vmax that is short of the absolute maximum possible amount for the individual volumes and to subsequently reduce the amount of Vmax over the course of the titration to a lower level V'max and, in certain cases, to further reduce the amount within a predetermined time period to a level of V"max. However, it is also possible to maintain the level of Vmax over the time periods t1 and t2 and then switch immediately to V"max. It has been found that the best choice is a reduction of the increment to a volume V"max that is below 50% Vmax as shown in the diagram. Values between 20% and 40%, and particularly a value of 30%, have proven to be most advantageous.

As can be seen in the diagram, this procedure results first of all in much smaller fluctuations of the volume difference during the titration time t1. Consequently, the titration process is more efficient, i.e., faster and more accurate because there is no longer a risk of over-titrating. At the same time, the lower limit for the individual volume per increment is set by the line Vmin. It has been found that through measures of this type, the titration time can be reduced to as little as 50% of the amount of time that would be required without the benefit of the invention and that this is accomplished not only without any loss but rather with a gain in accuracy.

The amount Vmin is always the smallest possible increment, e.g., 0.5 $^\mu$l, but the amount for Vmax, because it has a great influence on the course of the titration, is selected depending on the respective titrant. Generally, the selection of the individual quantities will range from 2 to 12 $^\mu$l. Within this range, e.g., for one-component titrants such as methanol or ethanol, it may be 5 to 8 $^\mu$l, for pyridine 3 to 4 $^\mu$l, and for a ketone, it will be in between at 4 to 5 $^\mu$l. The situation is analogous for two-component titrants, where the conventional quantities are between 8 and 20 $^\mu$l, most often between 8 and 12 $^\mu$l, with pyridine at 5 to 6 $^\mu$l again significantly below the general level.

The Vmax-factor, i.e., the degree of reduction involved in the transition to the second value V'max or V"max, will in most cases be around 30%, as has been mentioned above, but it also depends on the initial choice of Vmax. The larger Vmax is selected, the smaller will be the value to be chosen for the Vmax-factor, although the range of variation is not particularly large. For example, if Vmax is 8.0 $^\mu$l, a practical choice for the Vmax-factor is about 35%, i.e., between 30% and 40%, so that the mean deviation from the standard 30% value is only about 5%. As another example, with a Vmax-value of 10.0 $^\mu$l, the practical choice for the Vmax-factor is about 25% to 30%, i.e., only 5% below the standard 30%-mark. With 12.0 $^\mu$l, the range for the Vmax-factor is also between 20% and 30%. However, there is an upper limit for the choice of the Vmax-factor, because otherwise there will be a risk of over-titration.

Figure 1:
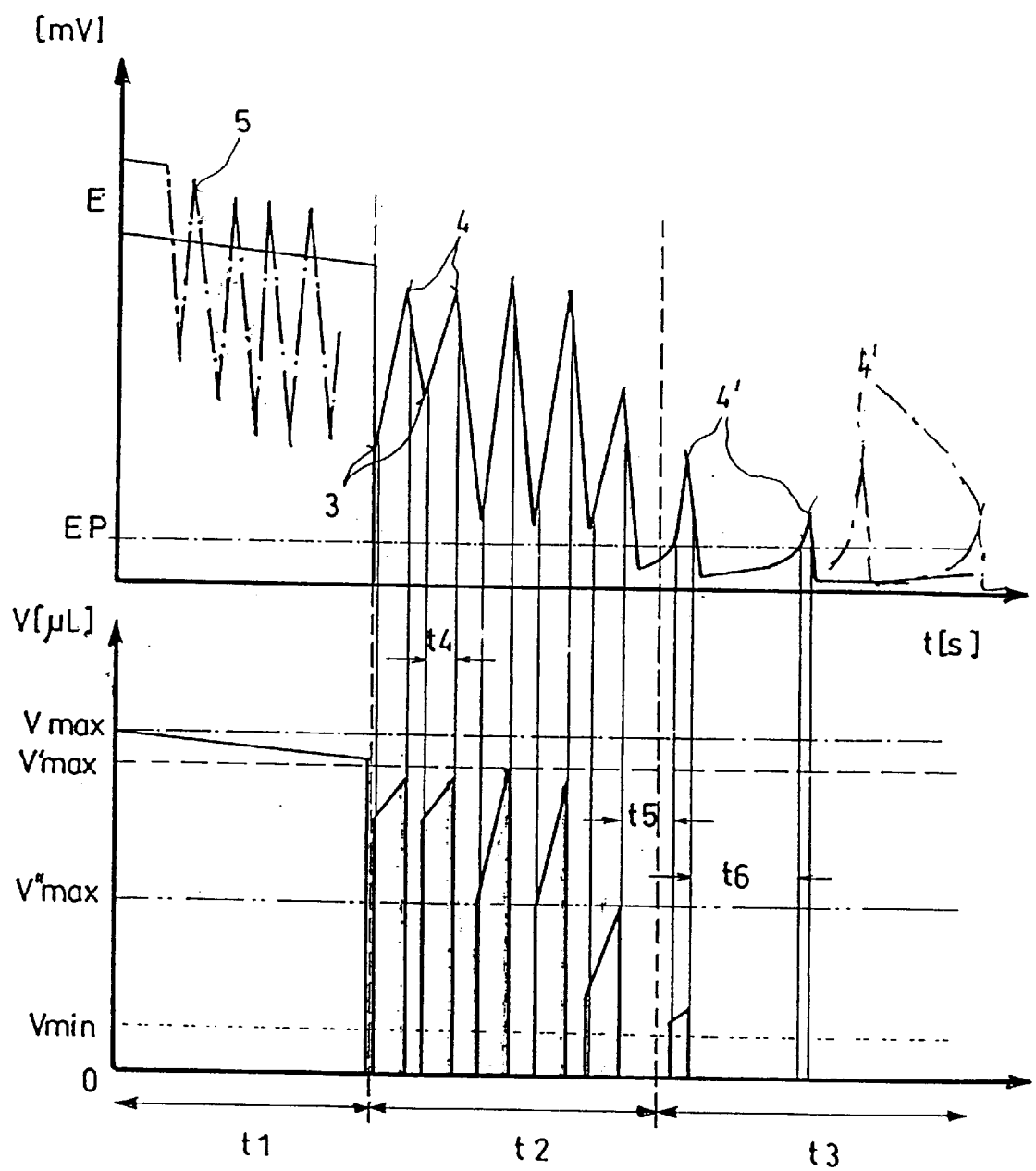
FIG. 1 represents a diagram to visualize the course of events in a titration process performed in accordance with the invention.

Not until the curve 1 or 2 (FIG. 2) takes on a stronger downward trend will fluctuations start to occur in which dips 3 alternate with peaks 4 (FIG. 1). The reason for the dips is that the reaction has at this point slowed down to the point where every addition of titrant will at first cause a decrease of the electrode voltage E, but subsequently the need for more titrant will resume. Titrant is added in this process in approximately constant time intervals t4 that can in some cases be somewhat longer than in the time period t1, so that the titration is accelerated during the time period t1.

It needs to be emphasized that the selection of the preset value of a maximum individual volume that is less than the absolute maximum possible value has a critical influence on the process (given that the combined volume of all increments is used to determine the water content of the respective sample in the customary manner). If, e.g., the selected value for Vmax is too large, the resulting problems will be similar to those observed in the prior-art methods. This case is illustrated in the upper diagram of FIG. 1 through the dash-dotted curve 5, of which the beginning and end are drawn in the diagram. As can be seen, the fluctuations begin at a far earlier time, which creates the risk of over-titrating. It is also possible that the "recovery cycle" will take longer, a situation that is visualized at the right-hand end of the curve 5.

In order to avoid over-titrating, the reduction from Vmax to V'max or V"max is made the first time after a strong dip 3 (fast reaction) has occurred in response to the addition of an increment of the given amount Vmax or V'max, respectively. A "strong" dip in this context is to be understood as a relative measure in comparison to smaller dips that may have preceded the strong dip. This is important, because an over-titration would cause the result to be in error on the high side. Thus, the most immediate benefit of limiting the maximum volume is a higher level of accuracy, which is particularly important in the case of a Karl Fischer titration. Over a subsequent time phase t2, the initial maximum volume is reduced to a lower maximum volume V'max, and in some cases it is further reduced to V"max. This method of reducing the maximum volume provides a better control over the problem of over-titration.

However, as another choice for the control variable, it is also possible to vary the time interval between the addition of successive increments, as has already been mentioned. While uniform intervals t4 are provided in the time phase t2, the reaction progressively approaches its end point according to the curves 1 and 2 (FIG. 2). With the approach towards the end point, the reaction also slows down. In response to the situation, the intervals can be extended to a longer value t5 during a next time period t3. In some cases, the intervals can be further lengthened to t6. The lengthening of the intervals avoids the risk of "after-consumption" that is feared by practitioners in the field of titration, because it occurs only after the termination of the measurement and falsifies the result. The method of lengthening the intervals allows the later occurring peaks 4' to be included in the measurement. Of course, this procedure is possible only if one takes the characteristic shape of the curves 1 and 2 (FIG. 2) into account by "predicting" their rate of decline, i.e., by taking the corresponding differential component into account for controlling the process. This contrasts with the prior practice in which only the distance from the end point EP (FIG. 1) at a given time went into the control function. As can be seen, the last of the indicated peaks 4' corresponds to the minimum volume Vmin that is still added at the end.

Figure 3:
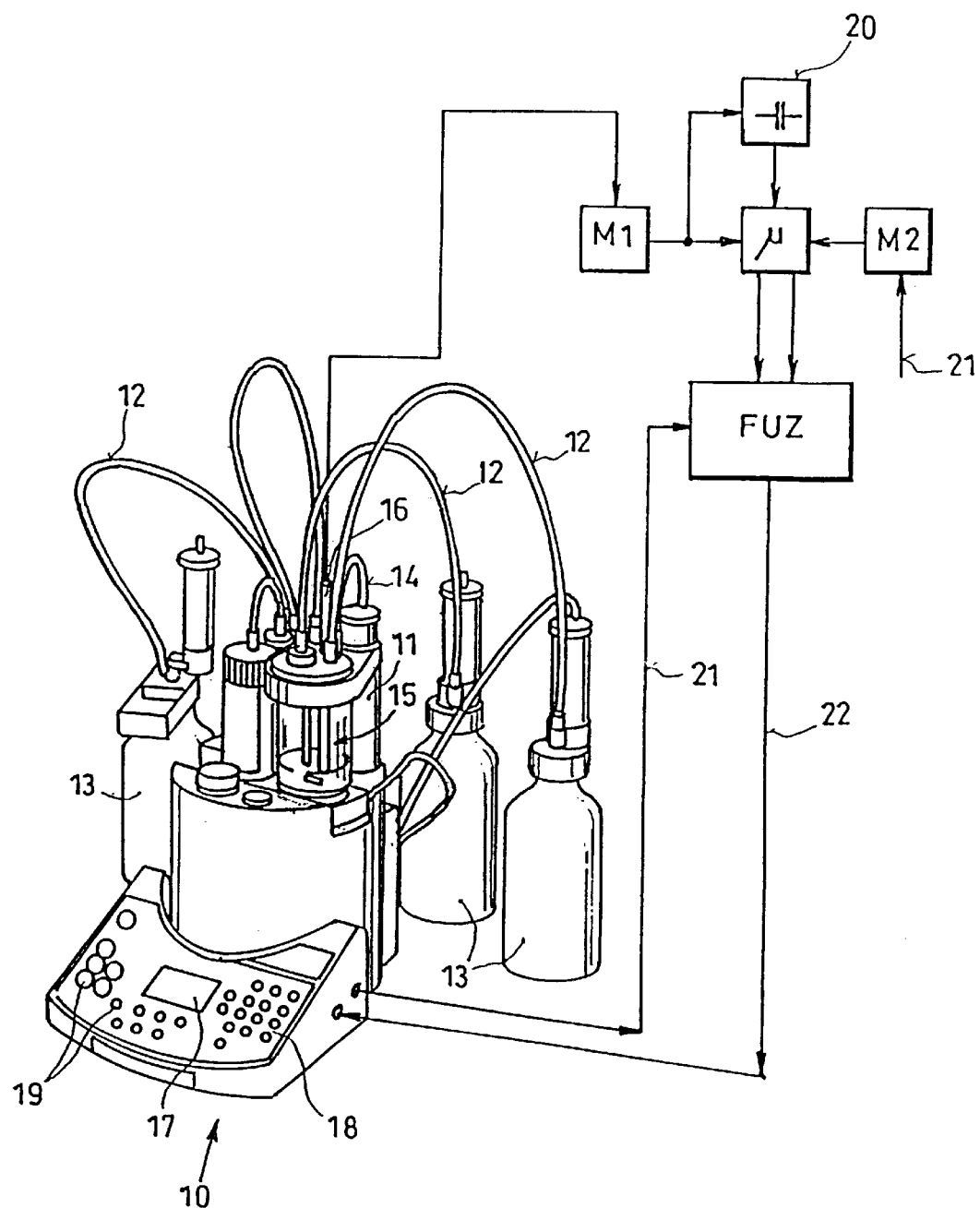
FIG. 3 represents an embodiment of a circuit schematic in accordance with the invention, including the apparatus.

FIG. 3 will serve to explain the best way of taking into account all of the different parameters in a titration apparatus by using the procedural steps that have been explained above. It is to be understood that FIG. 3 represents only one among many conceivable embodiments, and possible variations and further developed versions will also be mentioned. Although the embodiment of FIG. 3 is represented with block modules, it can also be realized advantageously by means of an appropriate software program.

Attached to a titration apparatus 10 is at least one burette 11 that is connected to a reagent bottle 13 through one of the hoses 12 for the delivery of titrant. The components 11 through 13 may be called the delivery unit. The titrant is delivered from the burette 11 through a further hose 14 to a titration vessel 15 that is sealed towards the outside and is appropriately equipped in the usual manner with a magnetic stirrer (not shown), preferably of a type with selectable stirring speed. In addition, the apparatus can include dryer tubes and other measures to prevent contaminants such as moisture (in the case of a Karl Fischer titration) from entering and falsifying the sample. The measurement is made, e.g., by inserting a polarized dual-rod platinum electrode 16 with an electrode pin distance of, e.g., 2 mm into the titration vessel 15. In addition, the standard arrangement also includes a pump for the delivery of the titrant. The titration apparatus 10 also has a display 17, a numerical keyboard 18, and control keys 19. All of these features are of a conventional nature and known to the practitioner in the field of titration.

FIG. 3 also includes a block diagram of a preferred embodiment of the inventive circuit that is a part the electronics portion of the apparatus 10. In accordance with the diagram, the signals generated by the electrode 16 (or, in other types of titration processes, the signal of a calorimeter, a photo-sensor element or the like) are first entered in an intermediate memory M1 or a sample-and-hold circuit. Its immediate function is to retain the current signal value. The current signal value can also be compared against the previously captured values in order to determine the corresponding differential component. However, in the present embodiment, the determination of the differential component is made in a separate differentiating stage 20, which delivers a corresponding signal to a processor $\mu$. The processor $\mu$ functions as a kind of comparator stage in this arrangement, because it also receives signals from a further memory M2 containing, e.g., the aforementioned empirically determined curves, so that additional factors such as the type of substance, level of concentration, type of titrant, type of solvent, electrode pin length, type of electrode, etc., are taken into account, each of which by itself will result in a different differential component (see curves 1 and 2 in FIG. 2). These curves are stored individually at different memory locations in the memory module M2 and are interrogated point by point over time in the course of the titration by means of the clock-pulse generator that is contained in the processor $\mu$.

It is possible, that at the same time the processor $\mu$ performs a comparison between the output signal of the differentiating stage 20 and the current signal of the memory module M2 in order to detect possible irregularities or deviations. This information is then sent through one of the output leads of the processor $\mu$ either directly to the apparatus 10 to indicate an alarm (e.g., "titration vessel not shut tight" or the like) or it is sent indirectly via a fuzzy logic module FUZ. Of course, it is also possible that a solvent or a substance does not correspond exactly to the curves stored in memory, in which case the processor $\mu$ can obtain a correction signal from the comparison with the output signal of the differentiating stage 20, which allows, e.g., to make a correction for the so-called drift errors.

The fuzzy-logic module FUZ itself can receive a number of different input signals. First of all, it receives information in a parallel or serial mode from the processor $\mu$ about the current distance of the curve from its endpoint. When the processor $\mu$ determines this information, the comparison with the curves stored in the memory module M2 may likewise be useful. In addition, the fuzzy-logic module FUZ also receives information or a signal from the processor µ about the current value of the differential component. Finally, the keypads 18 and 19 through an associated signal connection 21 allow additional data to be entered into the fuzzy-logic module FUZ for processing. The signal connection 21 may also be connected to the memory module M2 for the purpose of modifying or entering data about titration curves, as is indicated in FIG. 3. However, as an alternative, the memory module M2 can also be connected via the processor µ or in addition to it to the fuzzy-logic module FUZ, in order to deliver input signals to the latter. The fuzzy logic FUZ then ties all of the input values together and sends a corresponding control signal via an output connection 22 to the titration apparatus 10 to regulate the rhythm of the pump supplying the titration vessel 15 and/or to regulate the maximum volume (in accordance with the preceding explanations in the context of FIG. 1) as control variables.

The following examples will serve to further clarify the invention:

EXAMPLE 1

A titration was performed essentially as described above in the context of FIG. 1, except that approximately at the end of the time period t2 the volume was switched from Vmax directly to V"max=30% of Vmax. First, six samples were tested with a one-component titrant in order to determine the amount of time required for the titration. Then, for comparison, six additional samples were titrated in the conventional manner. It was found that with an average water content of 5983 ppm the titration ran 10% to 30% faster with the inventive process. Also, the accuracy was higher with the inventive process, because the results had better reproducibility.

EXAMPLE 2

Following the same procedure as in Example 1, two groups of 12 samples each with an average water content of 6132 ppm (as determined by the experiment) were analyzed by means of a two-component titrant. As in the case of Example 1, accuracy and reproducibility were improved, but most impressive in the outcome of the experiment was the fact that the results were obtained in as little as half the time it took with the conventional method.

EXAMPLE 3

While the water content that had to be measured was relatively high in Examples 1 and 2, the next experiment was to determine relatively small levels of water content, with the reproducibility of the results being the primary focus of the investigation. Using toluol in five samples, an average water content of only 115 ppm (560 µg) was determined with a titrant consumption of 0.3 mL and a deviation of s=0.119 ppm or 0.1%, a level of reproducibility that could not be achieved with the conventional method.

EXAMPLE 4

The next test involved the measurement of an even lower water content, using toluol in six samples. The average water content was 13.7 ppm (35 µg), albeit with a higher deviation of s=0.557 ppm or 4.1%. The amount of titrant consumed was 0.018 mL.

EXAMPLE 5

In this example, the objective was to measure the influence of the electrode pin length in the case of a two-component titrant.

It was found that with electrode pins of different lengths of 2 to 5 mm and with preset amounts of Vmin=0.0005 mL, Vmax=0.08 mL and a Vmax-factor of F=40%, it was possible to lower the titration time of 10 samples with an average water content of 7202 ppm and a deviation of only 0.14% from 47 seconds to 30 seconds, from 65 to 43 seconds, and from 96 to 55 seconds, i.e., the inventive process allowed the titration time to be reduced to less than ⅔ of the time required with the conventional process. Accuracy and speed were hardly influenced at all by the electrode pin length.

It was now attempted to further shorten the titration time by setting a relative drift stop of 40 µg/min. This resulted in a reduction of the titration time of about 50% in comparison to the state of the art, i.e., with 12 samples of 6132 ppm average water content and 0.06% deviation the titration time was 26 seconds vs. 54 seconds for the state-of-the-art method, and in another case it was 62 vs. 90 seconds. In this experiment, too, the electrode pin length in a range between 2 and 5 mm had no influence on accuracy and speed. Instead of a relative drift stop it would also be feasible to select an absolute drift stop, if desired.

EXAMPLE 6

In a further experiment in which one-component titrants were tested with electrodes of 2 to 5 mm pin length, it was found that the pin length had a strong influence, with shorter electrode pins performing markedly better. The best results were obtained with a 2 mm electrode pin, which had virtually no tendency towards oscillation. At the beginning, when there was a relatively high degree of difficulty involved in working without the fuzzy logic, the phenomenon was more closely investigated. It was found that in the presence of oscillations, the waiting times tend to increase gradually. The titration was started by adding increments of titrant at time intervals of t4=0.1 seconds. Various experiments indicated that, with the use of the fuzzy logic, after a waiting period (t1+t2) of 5 seconds the time interval needed to be switched to t5=0.5 seconds, and after an additional waiting period to t6=1 sec. This measure considerably alleviated the difficulties.

The details of the experiment were as follows: A Vmax-factor of 100% was used, i.e., the increment was switched from Vmax directly to Vmin (=V'max). On average, a water content between 5970 and 5977 ppm was measured. Using an electrode pin length of 2 mm and varying the time period after which the switch was made from a 0.1 second interval to a 0.5 second interval, the following values were obtained for the remaining time period.

TABLE 1

| Switch from 0.1 to 0.5 sec intervals after [min:sec] | Remaining time period at the 0.5 sec rate. [sec] |
| --- | --- |
| 1:37 | 60 |
| 1:23 | 42 |
| 1:25 | 53 |
| 1:23 | 30 |

By switching to a longer time interval, i.e., from t4 to t5 or t6, a premature termination of the titration with an apparent result that is too low is avoided. The premature termination of the titration occurs because the speed of the reaction decreases markedly towards the end of the titration and the apparatus does not recognize that the reaction is continuing if the time interval is too short. This illustrates the principal idea that sets the invention apart from the prior art, i.e., the inventive idea is to follow the course of the reaction curve more closely than is the case in state-of-the-art methods in which only the ordinate of each respective point along the curve 1 or 2 was used as control variable.

EXAMPLE 7

A sample of the same kind as in Example 6 was tested with a one-component titrant (pyridine). Vmin was set at 0.5 "L, Vmax at 5.0 "L, and the Vmax-factor at 100%, i.e., after a time period t2 the increment was switched directly from Vmax to Vmin=V'max. The result was in accordance with Table 1.

What is claimed is:

1. A process for titrating a substance comprising:
   (a) adding to the substance by stepwise addition an individual quantity of a titrant in given time intervals (t4, t5, t6), thereby to defme a speed of titration;
   (b) generating a titration curve as a result of the reaction between the substance and the titrant;
   (c) monitoring the titration curve in its approach toward an end point (EP) to produce a differential component; and
   (d) producing by means of a fuzzy logic (FUZ) responsive to said differential component a control function for regulating the addition of the titrant to the substance.

2. The process according to claim 1, wherein at least one of the parameters that define the speed of titration is varied over time by the fuzzy logic.

3. The process according to claim 2, wherein for fast reactions the individual quantity is the parameter being varied and for slow reactions the time interval (t4, t5, t6) is the parameter being varied.

4. The process according to claim 3, wherein a maximum volume (Vmax) is set for the individual quantity and the maximum volume is reduced at least once to a lower value (V'max, V"max) during the titration.

5. The process according to claim 4, wherein the maximum volume is reduced after a strong dip has occurred in the titration curve.

6. The process according to claim 4, wherein V'max is not more than 50% of Vmax.

7. The process according to claim 6, wherein V'max is between 20% and 40% of Vmax.

8. The process according to claim 7, wherein V'max is 30% of Vmax.

9. The process according to claim 1, wherein the differential component is derived at least in part from the titration curves that are characteristic of different substances, titrants, solvents, and electrode pin lengths.

10. The process according to claim 1, wherein at least the differential component and a momentary value of a distance from the end point (EP) are taken into account by the fuzzy logic (FUZ).

11. The process according to claim 1, wherein a maximum drift value is selectable and the titration is terminated when the maximum drift value is exceeded.

12. The process according to claim 1, wherein said process is used to perform a Karl Fischer titration and the differential component is obtained from a change in an electric potential.

13. Apparatus for titrating a substance comprising:
    (a) a titrating vessel (15) containing a substance to be titrated;
    (b) delivery means for supplying to said vessel by stepwise addition at given time intervals (t4, t5, t6) an individual quantity of a titrant;
    (c) means (M1) for generating a titration curve as a result of the reaction between the substance and the titrant;
    (d) means (20) for monitoring said titration curve in its approach toward an end point (EP) to produce a differential component; and
    (e) means including a fuzzy logic (FUZ) responsive to said differential component for producing a control function to regulate the addition of the titrant to the substance.

14. The titration apparatus according to claim 13, wherein the differentiating arrangement comprises a memory (M2) for storing at least two titration curves corresponding to different parameter selections.

15. The titration apparatus according to claim 13, comprising a fuzzy-logic stage (FUZ) equipped to receive the differential component as an input.

16. The titration apparatus according to claim 15, wherein the fuzzy-logic stage (FUZ) is further equipped to receive the momentary value of the distance from the end point (EP) as an input.

17. The titration apparatus according to claim 13, wherein said apparatus comprises means for connecting the differentiating arrangement to an electrode for determining a change in an electric potential for the purpose of performing a Karl Fischer titration.

* * * * *

UNITED STATES PATENT AND TRADEMARK OFFICE
CERTIFICATE OF CORRECTION

PATENT NO. : 6,372,505 B1 Page 1 of 1
DATED : April 16, 2002
INVENTOR(S) : Albert Aichert et al.

It is certified that error appears in the above-identified patent and that said Letters Patent is hereby corrected as shown below:

<u>Title page,</u>
Item [73], change the name of the Assignee to read:

-- Mettler-Toledo GmbH --

Signed and Sealed this

Tenth Day of September, 2002

Attest:

Attesting Officer

JAMES E. ROGAN
*Director of the United States Patent and Trademark Office*